CHRYSANTHEMUM PLANT
Filed Jan. 21, 1974
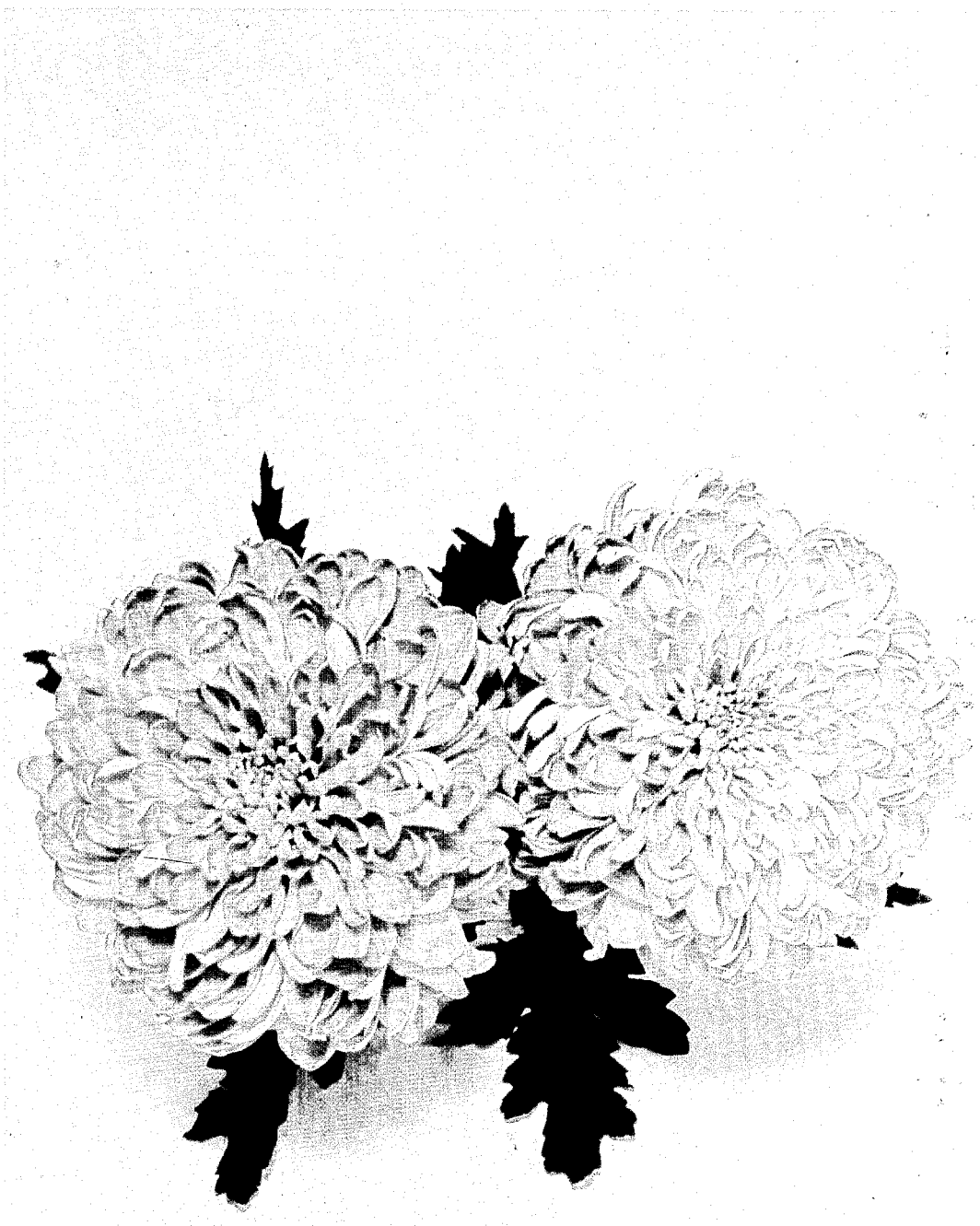

United States Patent

Plant Pat. 3,760
Patented Aug. 12, 1975

3,760
CHRYSANTHEMUM PLANT

Grace Y. Nakano, 1166 Bryant Ave.,
Mountain View, Calif. 94040

Filed Jan. 21, 1974, Ser. No. 435,321
Int. Cl. A01h *5/00*
U.S. Cl. Plt.—79 1 Claim This invention relates to a new and distinct variety of Chrysanthemum plant which is a sport of Dark Pinnacle, Ser. No. 392,953 and filing date Aug. 30, 1973.

This sport was selected from a flowering in my commercial greenhouses in Mountain View, Calif., because of its bronze color as compared to Dark Pinnacle which is a dark pink color. The plant was revegetated and through repeated flowering, the growth and response time proved to be the same as Dark Pinnacle. Flowering during the heat of summer resulted in a lighter bronze color.

This new sport is similar to Dark Pinnacle in the following characteristics:

1. Foliage,
2. Size of flower,
3. Heavy stem and growth,
4. Short growth, and
5. Flowering response.

This new selection is different from Dark Pinnacle in the following way: Bronze color.

Asexual reproduction of my new and distinct variety has proven to be consistent in:

1. Vegetative growth, and
2. Claims of flower characteristics.

The overall growth characteristics may vary according to environmental conditions under which it is grown, however, here in the Bay Area of California it has a response period of approximately seven and one-half (7½) weeks and is suggested for blooming from October through June.

The accompanying drawing illustrates the color as being as true as possible with color illustrations of this type. The color of the new variety will be apparent in the photograph.

The color designation is by use of the Royal Horticulture Society color chart, R. F. Wilson, of the Royal Horticulture Society of London, England.

Plant:

Botanical classification: *Chrysanthemum morifolium* Ramat.

Origin: Selected from a flowering in commercial greenhouses.

Form: Herbaceous.

Height: 90 to 100 centimeters.

Growth: Strong; vigorous; upright.

| | Dark Pinnacle | Bronze Pinnacle |
|---|---|---|
| Leaf: | | |
| Size | 16.2 cm. x 10 cm. (avg.) | 16.2 cm. x 10 cm. (avg.). |
| Shape | Ovate, deeply lobed | Ovate, deeply lobed. |
| Texture | Smooth, finely pubescent. | Smooth, finely pubescent. |
| Ribs and veins | Prominent | Prominent. |
| Margin | Deeply lobed | Deeply lobed. |
| Color | Yellow Green, 147/A | Yellow Green, 147/A. |
| Bud: | | |
| Diameter | 3.4 cm | 3.4 cm. |
| Depth | 2.5 cm | 2.5 cm. |
| Color | Red Purple, 74/D | Greyed-Orange, 168/D. |
| Flower color: | | |
| Center of flower | Red Purple, 73/D | Yellow Orange, 21/D. |
| Base of petal (¼" from end). | Red Purple, 74/D | Greyed Red, 179/D. |
| Inside of petal | Red Purple, 74/B | Gray Red 179/B. |
| Reverse of petal. | Purple, 75/C | Yellow, 11/C. |
| Tonality from distance. | Red Purple, 74/C | Orange Red, 34/D. |
| Other characteristics: | | |
| Size of flower | 13.5 cm. x 8.84 cm | 14 cm. x 9 cm. |
| Stamens | Numerous | Numerous. |
| Pollen | None visible | None visible. |
| Pistil | Present | Present. |

I claim:

1. A new and distinct variety of Chrysanthemum plant having the characteristics of a bronze flower.

No references cited.

ROBERT E. BAGWILL, Primary Examiner